United States Patent [19]

Forte

[11] Patent Number: 5,236,461
[45] Date of Patent: Aug. 17, 1993

[54] TOTALLY POSTERIOR STABILIZED KNEE PROSTHESIS

[76] Inventor: Mark R. Forte, 11 Oak La., Pine Brook, N.J. 07058

[21] Appl. No.: 673,790

[22] Filed: Mar. 22, 1991

[51] Int. Cl.$^5$ .............................................. A61F 2/38
[52] U.S. Cl. .................................................. 623/20
[58] Field of Search ........................................... 623/20

[56] References Cited

U.S. PATENT DOCUMENTS

| | | | |
|---|---|---|---|
| 4,207,627 | 6/1980 | Cloutier | 623/20 |
| 4,298,992 | 11/1981 | Burstein et al. | 623/20 |
| 4,888,021 | 12/1989 | Forte et al. | 623/20 |
| 4,892,547 | 1/1990 | Brown | 623/20 |

Primary Examiner—Randy C. Shay
Attorney, Agent, or Firm—Klauber & Jackson

[57] ABSTRACT

A posterior stabilized knee prosthesis includes a femoral component formed by medial and lateral condyles, each having an anterior portion, a distal portion and a posterior portion, an anterior patella flange interconnecting the anterior portions of the medial and lateral condyles in parallel, spaced apart relation, and a cam member connected to the lateral surface of the posterior portion of the medial condyle and to the medial surface of the posterior portion of the lateral condyle and having a convex cam surface; a tibial component including a multi-radius medial and lateral tibial plateau bearing surfaces for receiving the medial and lateral condyles for rolling and sliding movement thereon, and a follower member positioned between the medial and lateral tibial plateau bearing surfaces for receiving the cam surface for rotational and sliding movement thereon; the cam surface being in contact with the follower member for substantially the entire flexion range of the knee, with the cam surface being in congruent contact with the follower member from approximately the end of posterior rollback at approximately 25°–30° of flexion to full-flexion; and the cam surface being in sliding contact with the follower member to provide the posterior rollback of the convex cam surface during flexion, starting at approximately −6° (hyperextension) of flexion and ending at approximately 25°–30° of flexion; and the cam member and follower member having heights which are not greater than the thickness of the condyles so as not to extend beyond the inner surfaces thereof.

46 Claims, 9 Drawing Sheets

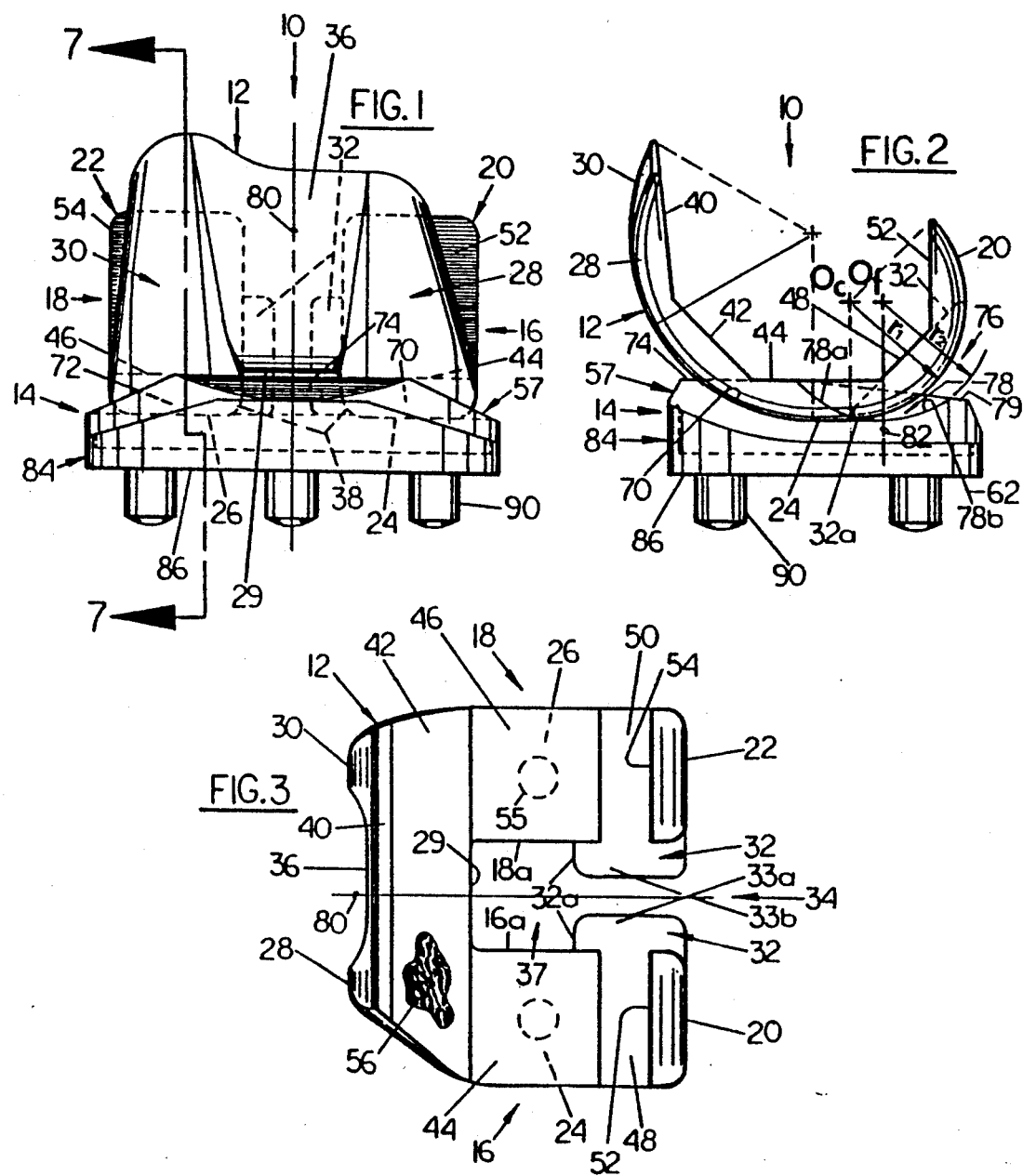

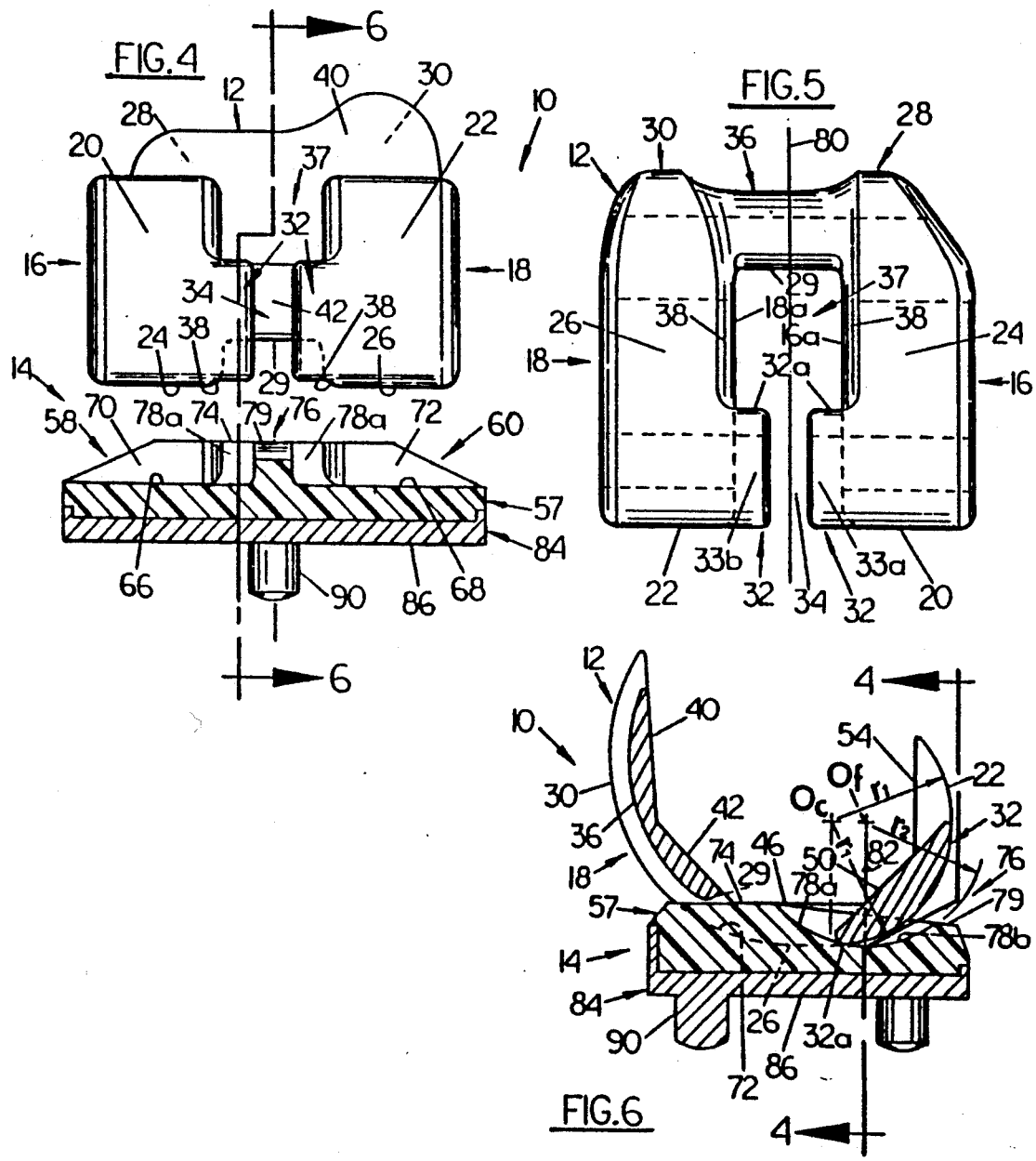

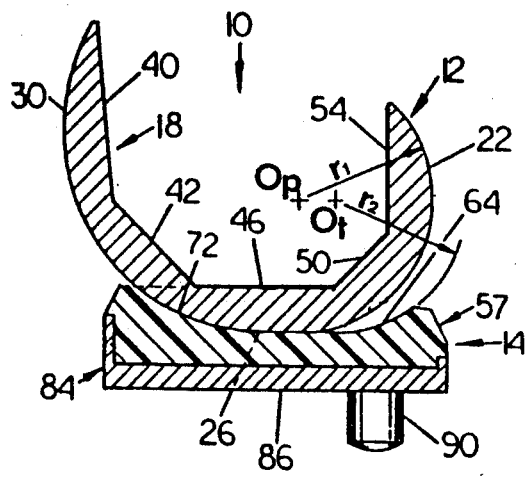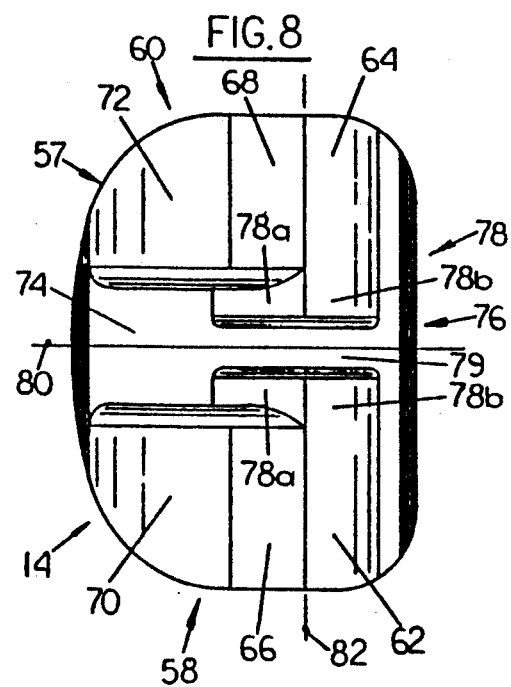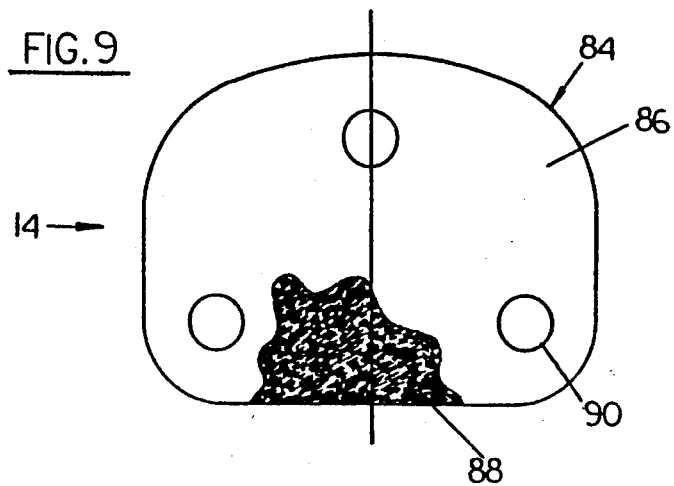

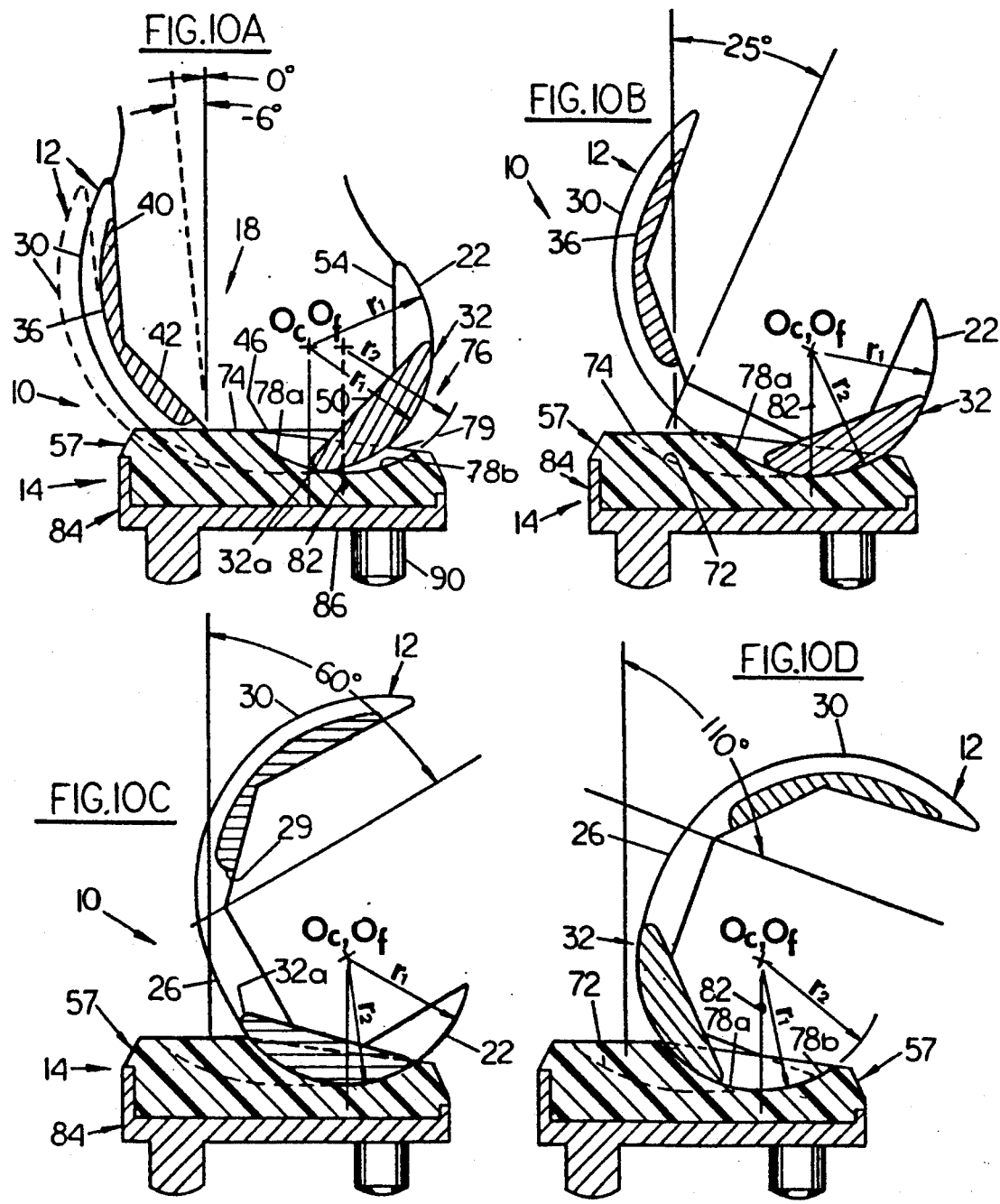

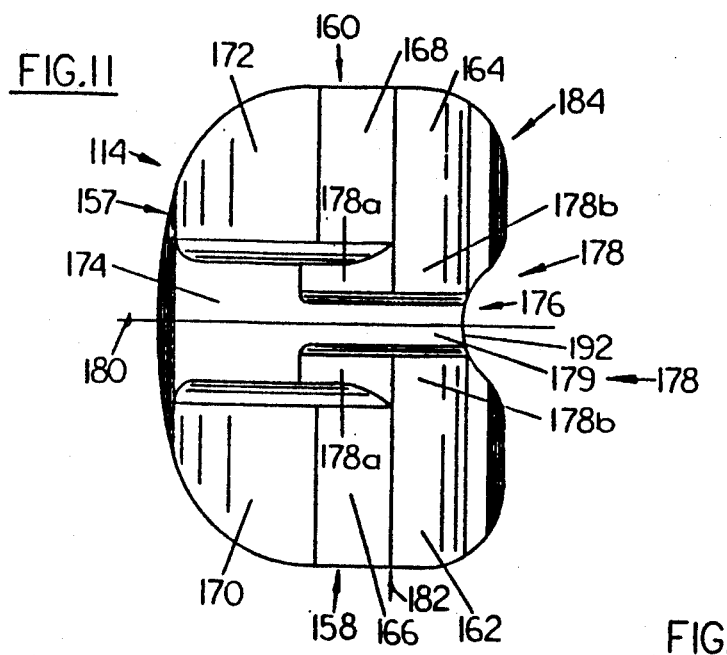

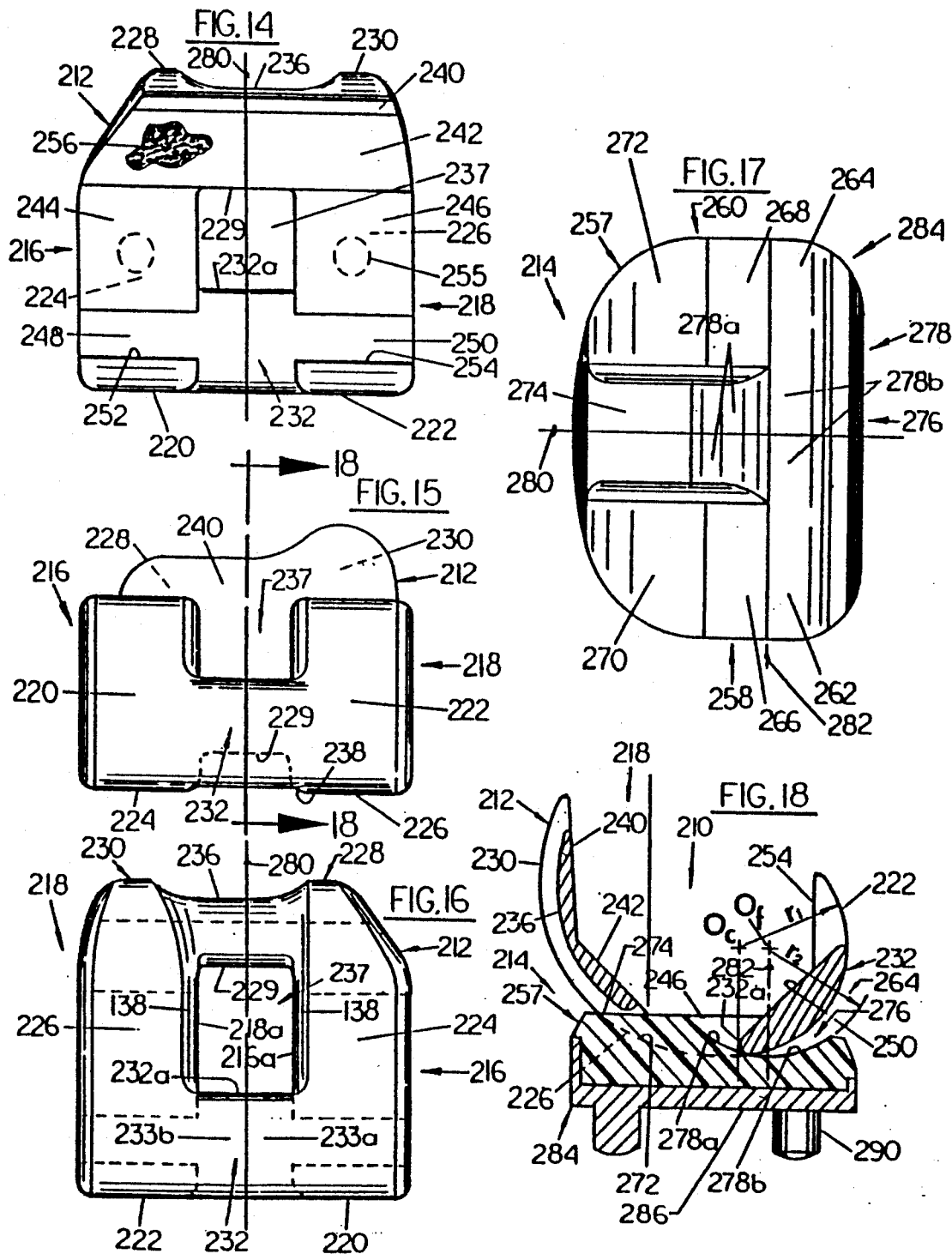

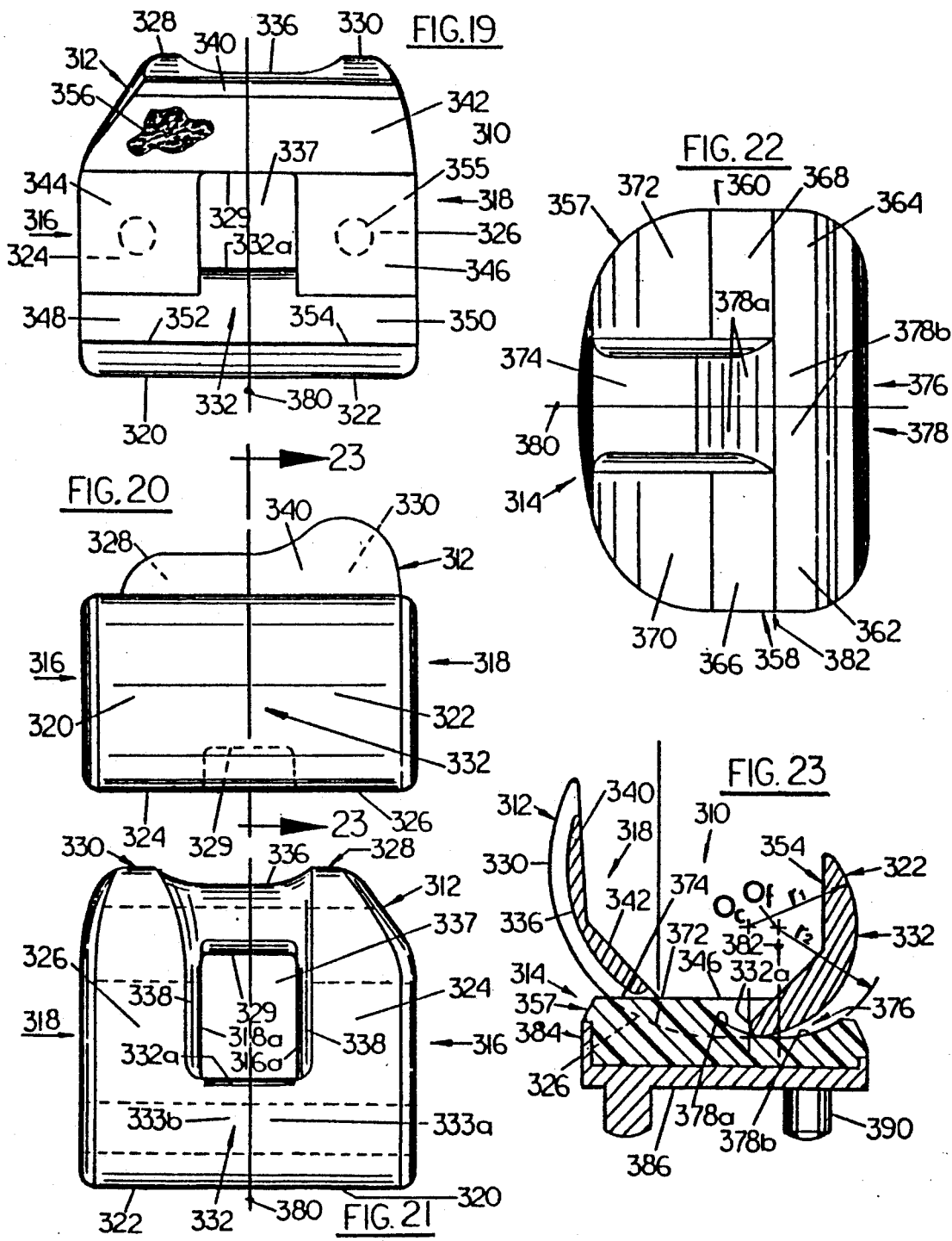

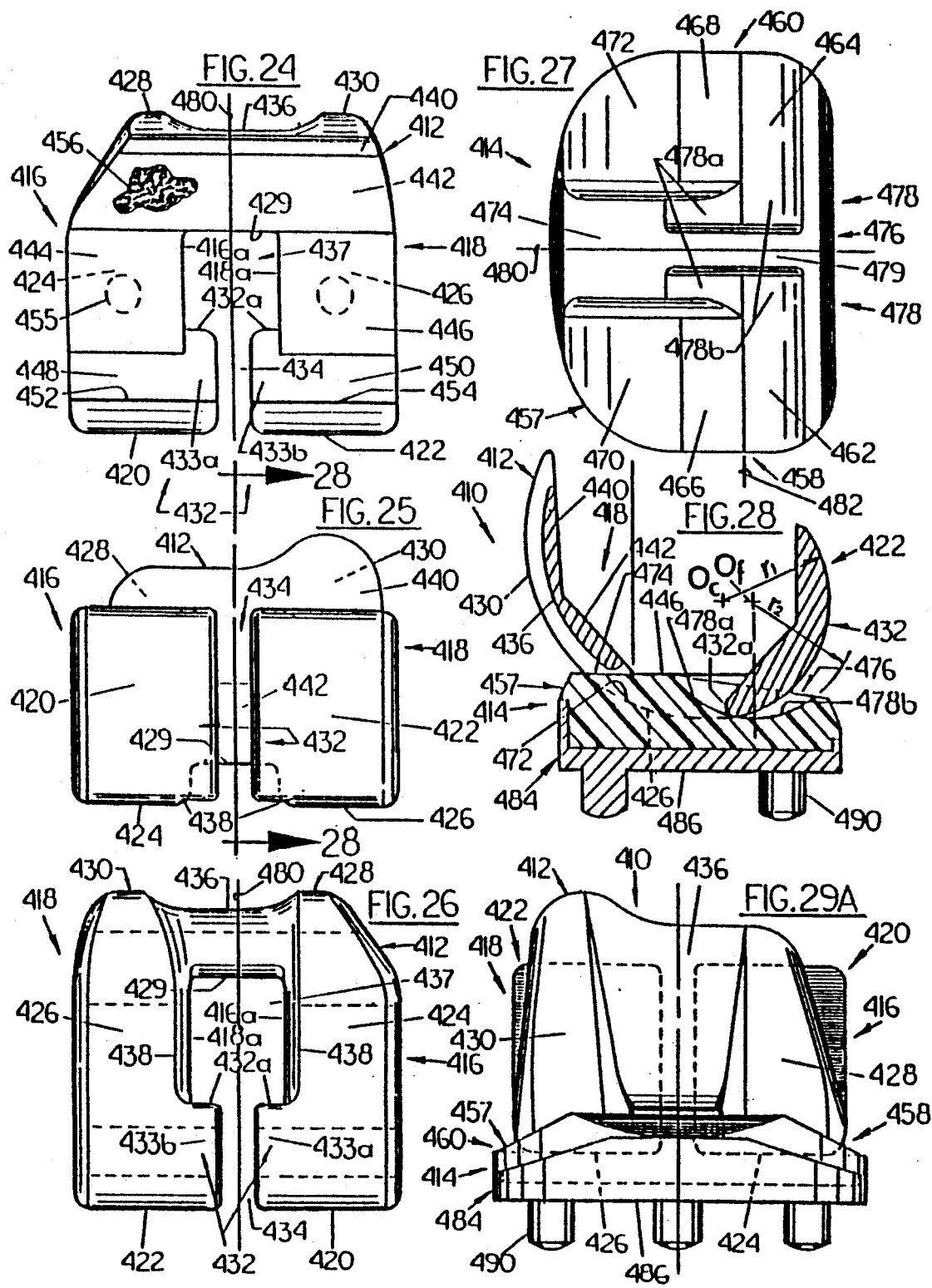

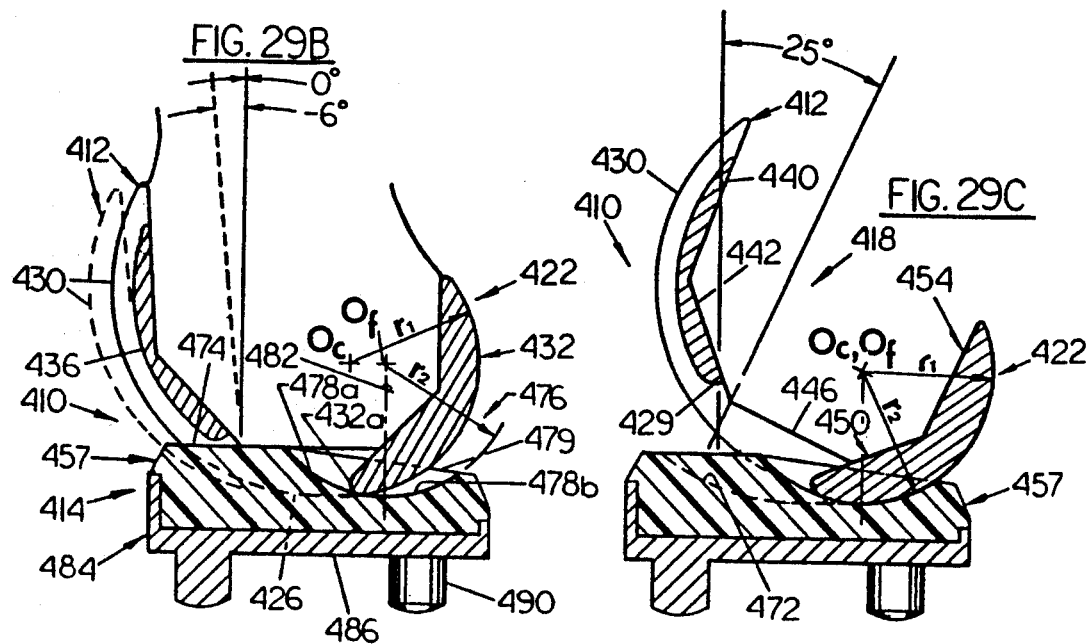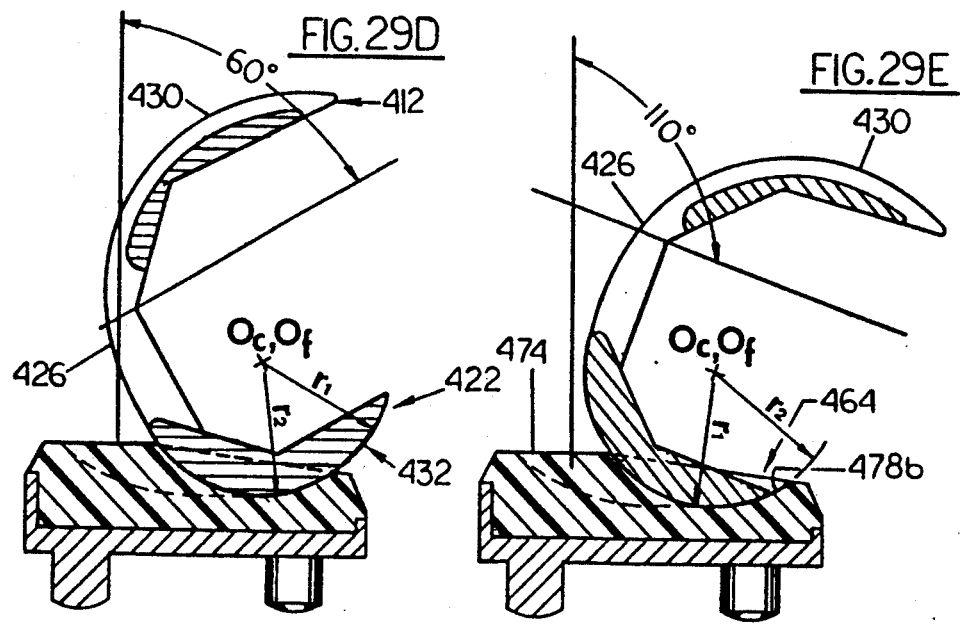

TOTALLY POSTERIOR STABILIZED KNEE PROSTHESIS

BACKGROUND OF THE INVENTION

The present invention relates generally to knee prostheses and, more particularly, to a posterior stabilized knee prosthesis which provides posterior stabilization of the reconstructed knee joint by means of a mechanical cam/follower mechanism as functional compensation for lost, resected or incompetent posterior cruciate ligament structures of the natural knee.

Known total knee prostheses can essentially be classified into three basic categories. In the first category, the articular surface of the distal femur and proximal tibia are "resurfaced" with respective metal and plastic condylar-type articular bearing components. These knee prostheses provide substantial rotational and translational freedom and require minimal bone resection to accommodate the components in the available joint space. The patella-femoral joint may also be resurfaced by a third prosthetic component, as well. The femoral, tibial and patella prosthetic resurfacing components are affixed to respective adjacent bone structure by a cementing or by a biological bone ingrowth fixation means.

The femoral component is of metallic alloy construction (cobalt-chrome or 6A14V titanium alloy) and provides medial and lateral condylar bearing surfaces of multi-radius design of similar shape and geometry as the natural distal femur or femoral-side of the knee joint. The tibial component can be made entirely of plastic (UHMWPE:ultra-high molecular weight polyethylene) or comprised of a metallic base component and interlocking plastic component. The plastic tibial bearing surface is of concave multi-radius geometry to more or less match the mating femoral condyles, depending upon the design levels of primary and secondary articular constraint. Both the femoral and tibial components are independently positioned on either side of the knee joint and are not mechanically connected or linked together, as in the case of constrained or hinged type of knee prostheses, which constitutes the secondary category of total knee prostheses.

In resurfacing types of total knee prostheses according to the first category, the tibial bearing surface geometry can assume a variety of configurations, depending upon the desired extent of articular contact congruency and associated translational (medial-lateral and anterior-posterior) and rotational (axial and varus-valgus) secondary femoro-tibial motions. These various secondary motions allow the resurfaced knee to function in a natural-like biomechanical manner in conjunction with the surrounding ligamentous and muscle structures about the knee joint. The soft tissue structures maintain the femoral and tibial bearing surfaces in contact, provide the necessary levels of force constraint to achieve knee joint stability, and functionally decelerate the principal motion in flexion-extension and secondary motions, such as axial rotation, in a controlled manner. Additionally, this functional interaction between the surrounding tissue structures and the implanted knee prosthesis minimizes abrupt motion stoppage or impact loading of the prosthetic articular surfaces, thus preventing overstressing at the component fixation interface. Examples of resurfacing types of total knee prosthetic devices are disclosed in U.S. Pat. Nos. 3,774,244 to Walker; 3,728,742 to Averill et al.; and 4,207,627 to Cloutier.

On the other hand, the mechanically linked, constrained or hinged type of knee prosthesis according to the second category provides a fixed fulcrum flexion-extension capability. The "hinged knee" therefore is usually surgically indicated in selected cases where the surrounding soft tissue structures are grossly degenerated and incapable of providing functionally acceptable knee joint stability. An example of this type of total knee prosthetic device is disclosed in U.S. Pat. No. 3,996,624 to Noiles.

In clinical situations where prosthetic knee joint reconstruction is surgically indicated in the presence of compromised posterior (tibial) stability, that is, due to absent or incompetent posterior cruciate ligament structures, a posterior-stabilized total knee device can be utilized. This type of device constitutes the third category of total knee prosthetic devices. The posterior-stabilized total knee devices essentially incorporate all of the functional features of the first category, that is, the resurfacing condylar-type of knee prostheses, in addition to incorporating a mechanical cam/follower mechanism for providing posterior (tibia-to-femur) constrainment. The cam/follower mechanism is positioned within the intercondylar space of the femoral component and provides substitutional posterior constraint, as a predesigned compensation feature for lost posterior cruciate function or for compromised posterior knee stability. Thus, the possibility of anterior dislocation of the femur is reduced.

The cam portion of the cam/follower mechanism, generally includes a convex lobe shaped surface, integrally machined or cast within a box-like structure known as the "stabilizer box", located between the medial and lateral condyle runners of the femoral component and positioned between the anterior and posterior condyles. The cam surface is generally formed within the posterior wall portion of the stabilizer box and is bounded by the superior wall on the top, the medial and lateral wall portions on the sides and the anterior portion at the front. The stabilizer box structure, thus formed, occupies a significant envelope, relative to the overall dimensions of the femoral component and therefore, requires a substantial resection of viable bone to allow its accommodation within the intercondylar sector of the distal femur.

The posteriorly positioned articular convex surface of the cam is precisely ground and highly polished. The convex cam articulates with the anteriorly positioned and posteriorly oriented follower, as the knee undergoes femoro-tibial flexion and extension articulation. The mating follower surface is machined integral within the ultra-high molecular weight polyethylene (UHMWPE) tibial component. The follower member usually consists of a relatively concave articular surface located on the posterior side of an upwardly extending post-like structure, which is positioned between the concave medial and lateral tibial plateau bearing surfaces. The resultant action of the contacting cam/follower mechanism, thus described, provides posterior stabilization or constraint of the tibial component, relative to the femoral component: generally from about mid-range to full range of flexion. Within this limited range, therefore, the stabilizing mechanism essentially simulates the functional contribution of the natural posterior cruciate ligaments attached between the anterior femur and posterior tibia aspects of the knee joint. Additionally, since the cam/follower surface geometry is generally non-congruent, the mechanism can be designed to produce posterior roll-back of the femoro-tibial articular contact, simulating the natural biomechanical displacement characteristics of the natural knee.

Examples of posterior-stabilized total knee prostheses of the type described above, are disclosed in U.S. Pat. Nos. 4,209,861 to Walker; 4,298,992 to Burstein et al.; 4,213,209 to Insall et al.; and 4,888,021 to Forte et al. Each of the devices described in the above Patents incorporates a UHMWPE tibial component with a pair of medial and lateral concave plateau bearing surfaces and a metal alloy femoral component with mating multi-radius condylar runners which ride on the bearing surfaces. Both prosthesis surface geometries approximate the articular design of the natural knee. The articulation of the femoral condyles with the tibial plateau bearing surfaces allows primary femoro-tibial flexion and extension, and secondary (freedom) motions of axial and varus-valgus rotations and anterior-posterior and medial-lateral translations. The knee joint reaction forces during primary or secondary motion are principally supported by the tibial bearing surfaces, and to some extent by the cam/follower surfaces, and are transferred to the underlying fixation interfaces and adjacent supportive bone structures.

Additionally, the UHMWPE tibial component incorporates an upwardly extending post-like structure which is positioned between the plateau bearing surfaces, slightly anterior of the component mid-line. The generally concave follower surface is integrally machined on the posterior-side of the post. With the femoral and tibial knee components in a normally reduced, surgically implanted position, the upwardly extending tibial post extends into the stabilizer box structure located within the intercondylar space of the femoral component. Posterior tibial constraint is achieved when the posteriorly oriented face of the follower contacts the generally anteriorly oriented lobe surface of the cam.

Both the cam/follower articulation and the femoro-tibial articulation occur concurrently during knee flexion-extension. However, the commencement of cam/follower contact, and hence, commencement of posterior stabilization occurs on or about mid-flexion range for the devices described in U.S. Pat. Nos. 4,213,209 and 4,298,992 and near the onset of knee flexion for the device described in U.S. Pat. Nos. 4,888,021 and 4,209,861. However, as to the former Patents, it is noted that there are forces acting over the entire range of motion, which are not accounted for in these Patents.

Further, in each of the above devices, the existence of a relatively large stabilizer box at the mid-portion of the femoral component requires resection of a significant block of viable intercondylar bone to accommodate implantation of the femoral component prosthetic device. Additional surgical instrumentation is required and the surgical procedure is somewhat more complicated compared to a conventional condylar-type knee resurfacing device. Furthermore, in each instance, the stabilizer box member has medial and lateral side walls and anterior and posterior walls. These surfaces can contact the upwardly extending tibial post during inadvertent severe excursions of secondary knee motion, that is, axial and varus-valgus rotations and medial-lateral translation, and hence, can function to constrain these movements within certain limits, commensurate with design dimensional clearances. While these devices have been effective in constraining these types of motion excursions and therefore, effective in providing a high degree of controlled femoro-tibial stability, the resulting force reactions occurring between the stabilizer box surfaces and tibial post can produce periodic and severe (moment and torque) loading at the fixation sub-structure interfaces, which can cause complications related to component loosening.

Another type of posterior stabilized knee prosthesis is described in U.S. Pat. No. 4,892,547 to Brown. This design incorporates a cam/follower mechanism having a low profile and requires no resection penalty associated with the accommodation of a protruding stabilizer box structure. The heights of the tibial follower post (eminence) and femoral cam members are no higher than the thickness of the distal and posterior condyles of the femoral component. The required femoral resections are thus identical to that of a conventional resurfacing condylar-type of knee prosthesis of similar size and geometric design.

However, this Patent suffers from some disadvantages. First, although the relatively short extending tibial post is located between the plateau bearing surfaces, the cam member is integrally incorporated at a high position, between the posterior condyles of the femoral component. This knee device is therefore described as a "partially stabilized" total knee joint prosthesis, since the cam/follower mechanism only comes into contact after flexion of approximately 40° has occurred, and continues until full flexion is attained. Thus, there is no posterior constrainment of the tibia relative to the femur from maximum hyperextension at about −6° to approximately 40° flexion. In this regard, this knee device is similar, functionally, to other devices, such as those previously described in U.S. Pat. Nos. 4,213,209 and 4,298,992. This Patent therefore does not take into account the forces acting over the entire range of motion of the knee.

Secondly, when the cam follower first contacts the cam surface at approximately 40° flexion, there is initiation of mechanical posterior rollback due to the differences in articular curvature. In a normal knee, femoro-tibial rollback starts at the onset of flexion and is completed at approximately 25°–30° of knee flexion. This rollback provides substantially a purely rolling motion of the condyles on the tibial plateau bearing surfaces (femoro-tibial motion), and thereafter, there is a transitional motion of rolling and sliding. Therefore, it is desirable that the cam/follower contact point for start of rollback occur as early as possible in the flexion range and that completion of rollback occurs at or preferably before approximately 40° flexion. The device in U.S. Pat. No. 4,892,547 furthermore describes the action of the cam/follower mechanism in producing posterior roll-back, simulating the rolling-type of posterior displacement of the femoro-tibial articular contact in the natural knee, during knee flexion. However, in U.S. Pat. No. 4,892,547, the indicated commencement of this roll-back feature occurs when the cam/follower mechanism comes into contact at approximately 40° flexion and is completed after flexion to approximately 90°. In the normal knee, through the complex active interaction of the anterior and posterior cruciate ligaments and other structures, the rollback displacement of the point of femoro-tibial articulation commences early in the flexion range, as aforementioned, and is essentially completed prior to 40° flexion. The character of the primary articulation in flexion, after completion of the rollback stage gradually changes to a sliding and gliding mode in a manner approaching that of a fixed fulcrum posterior condyle rotation.

Third, the geometry or shape of the articular surfaces of the cam and follower members in U.S. Pat. No. 4,892,547 are not described as being congruent, and therefore, the functional contact area is small and the resultant contact stress high, when joint loading which tends to produce anterior dislocation of the femur, is imposed. Articular surface congruence of the cam and follower members is incorporated in the posterior stabilized device described in U.S. Pat. No. 4,888,021. However, this latter Patent utilizes the aforementioned box-like structure and requires a large resection area. The relative advantages of large contact areas associated with joint prosthesis of bearing congruency is frequently reported in the literature and has been adopted in a number of prosthetic devices for the knee joint, as well as, for other joints of the human body, that is, the shoulder and hip.

OBJECTS AND SUMMARY OF THE INVENTION

In view of the above, the present invention provides a posterior stabilized total knee prosthetic device, which provides posterior stabilization from the onset of femoro-tibial flexion (at full hyperextension) and continuing throughout the full flexion range.

Additionally, the selected geometry and position of the cam and follower members can produce a more natural-like posterior rollback displacement of the point of femoro-tibial articulation, commencing from the onset of flexion (at full hyperextension) and proceeding in a uniform manner to approximately 25°-30° flexion, where rollback is essentially completed. From this point in the flexion range, until full flexion is reached, the cam and follower members come into congruent contact, as does the femoro-tibial articulation between the femoral condyles and tibial plateau. In this manner, posterior stabilization continues to occur throughout the entire flexion range. After rollback is completed (after approximately 25°-30° flexion) the cam/follower mechanism assumes essentially the same geometric orientation, position and articular geometry as the femoral condyles and tibial plateau bearing surfaces, therefore, tending to functionally augment the transfer, sustainment and distribution of the knee joint forces imposed during knee flexion.

Additionally, from about 25°-30° flexion to full flexion, congruent contact of the cam-follower mechanism and the femoro-tibial bearing surfaces also provides anterior stability, thus reducing the possibility of posterior dislocation of the femur. In fact, as flexion increases, above the 25°-30° range, the net effective contact area of both the femoro-tibial bearing surfaces and cam/follower bearing increases proportionally, thus tending to provide increased contact area of all bearing surfaces at the higher levels of joint loading, associated with increased flexion.

The stabilizer cam and follower members are of low profile and are effectively contained within the thickness dimensions of the distal and posterior condyles. In this manner, the need for a stabilizer box is avoided, together with all of its associated potential shortcomings, as discussed previously.

Accordingly, it is an object of the present invention to provide a posterior stabilized knee prosthesis that provides posterior stabilization of the knee joint from the onset of flexion at hyperextension and throughout the complete range of flexion.

It is another object of the present invention to provide a posterior stabilized knee prosthesis in which the cam/follower mechanism produces posterior displacement or rollback of the femoro-tibial joint articular contact in a similar manner as the natural knee.

It is still another object of the present invention to provide a posterior stabilized knee prosthesis that provides congruent contact of the posterior stabilizer bearing surfaces.

It is yet another object of the present invention to provide a posterior stabilized knee prosthesis that functions in conjunction with the primary femoro-tibial articular mechanism in sharing and in distributing compressive knee joint forces.

It is a further object of the present invention to provide a posterior stabilized knee prosthesis that provides a counter force moment which tends to reduce the resultant tibial fixation interface moment resulting from the femoro-tibial joint reaction forces.

It is a still further object of the present invention to provide a posterior stabilized knee prosthesis that requires no additional femoral and tibial bone resectioning compared to a condylar-type resurfacing or non-posterior stabilizing-type of total knee prosthesis of similar size and design.

It is a yet further object of the present invention to provide a posterior stabilized knee prosthesis that more closely mimics the natural biomechanics of the knee joint as it relates to posterior rollback of the articular surfaces during flexion of the knee.

It is another object of the present invention to provide a posterior stabilized knee prosthesis in which the center and radius of curvature of the cam surface are the same as the center and radius of curvature of the posterior femoral condylar surfaces.

It is still another object of the present invention to provide a posterior stabilized knee prosthesis in which the cam follower is always in contact with the cam surface during the entire flexion range of the knee.

It is yet another object of the present invention to provide a posterior stabilized knee prosthesis in which the center and radius of curvature of the follower surface are the same as the center and radius of curvature of the posterior portions of the tibial bearing surfaces.

It is therefore an object of this invention to provide a posterior stabilized total knee prosthesis device offering the above features and associated, potential clinical advantages. These and other objects are achieved in a knee joint prosthetic device, which is comprised of a femoral component, a tibial component and patellar component, suitably designed to restore knee joint function when surgically implanted to the prepared ends of the femur, tibia and patella, respectively.

The femoral component incorporates a pair of lateral and medial condylar runners, which like the natural counterparts are spatially separated and are of multi-radius geometry. Furthermore, anterior portions of the condyles are integral with an interconnecting flange portion, which provides an articular femoral bearing surface for the resurfaced femoro-patella joint. In addition to the above features, the femoral component incorporates an integral convex shaped cam member at the intercondylar position, at essentially the junction between the distal and posterior portions of the condyles. The articular surface of the cam member is essentially integral to and has the identical center and radius of curvature as the posterior portions of the femoral condyles.

An intercondylar opening within the condyles is formed by the posterior edge of the distal portion of the patella flange at the junction of the anterior and distal condyles, the anterior aspect of the intercondylar stabilizer cam member, and the medial and lateral edges of the respective lateral and medial condyles. The boundaries of the opening are essentially within the plane and maximum thickness of the distal or posterior portions of the femoral condyles. However, an intercondylar stabilizer box which protrudes within the bone space of the distal femur and requiring a substantial removal of bone to provide the necessary clearance for implantation of the femoral component is not required by the present invention.

The tibial component incorporates medial and lateral concave tibial plateau bearing surfaces which are spaced consistent with the span of the femoral condylar runners to allow accurate mating and knee joint flexion-extension articulation. The follower member of the posterior stabilizer mechanism is integrally disposed within an interconnecting projection located between the plateau bearing surfaces, situated posterior of the tibial component mid-line. The anterior and posterior portions of the interconnecting projection extend into the intercondylar opening, but not above the thickness of the distal or posterior portions of the condyles of the femoral component. Since its maximum height is not greater than the thickness of the distal or posterior portions of the femoral condyles, resection of additional distal femur bone to provide adequate clearance for the height of the projection is, therefore, not required.

The articular surface of the follower member has an identical position, orientation, profile shape and radius of curvature as the medial and lateral posterior tibial plateau bearing surfaces. In the preferred embodiment, the anterior edge of the intercondylar cam member contacts the central/anterior aspect of the stabilizer follower surface at the onset of flexion (at hyperextension) of the knee joint and remains in contact as the flexion angle increases. Thus, posterior stabilization occurs over the entire flexion-extension range to prevent anterior dislocation of the femur in clinical situations where the surrounding adjacent ligamentous and muscle structures are compromised by trauma, disease or previous surgery. In an especially preferred embodiment, the radius of curvature of the cam member and follower member are identical but the centers of curvature are separated by some small distance.

The ensuing contact of the anterior aspect of the intercondylar (femoral) cam member and the central/anterior aspect of the (tibial) follower member also produces a camming action which displaces the center of curvature of the cam member, posteriorly and toward the center of curvature of the follower member, as the flexion angle increases, thus producing posterior rollback displacement of the condyles of the femoral component relative to the plateau bearing surfaces of the tibial component. At approximately 25°-30° flexion, the center of curvature of the cam member meets and coincides with the center of curvature of the follower member to complete posterior rollback of the femoro-tibial joint. Since the center and radius of curvature of the posterior condyles are coincident with the center and radius of curvature of the cam member and the center and radius of curvature of the posterior portion of the tibial plateau bearing surfaces are coincident with the center and radius of curvature of the follower member, both the femoro-tibial bearing surfaces and the cam-follower bearing surface coincidentally assume a condition of area-to-area or congruent articular contact after rollback is completed. From this point in the flexion range (25°-30°) to full-flexion, both articular elements will maintain contact congruency. The net area of contact of the cam-follower articular surface increases proportionally as flexion angle increases, reaching a maximum value at approximately 60° flexion. From this flexion level to full-flexion, the net contact area decreases to approximately half of the available surface area. In another preferred embodiment, the design of the cam member allows attainment and sustainment of maximum contact area of the cam-follower articular surface from approximately 25°-30° flexion to full-flexion.

Required bone resection at the anterior, distal and posterior aspects of the distal femur to allow accurate seating of the bone/femoral component fixation interfaces are identical with bone resections for a condylar resurfacing-type (unstabilized) total knee prosthesis of similar size and design configuration. This feature is provided since the height of the cam and follower members of the stabilizer mechanism, which is contained within the intercondylar space, is designed to be no greater than the maximum thickness of the distal and posterior portions of the condyles of the femoral component. The resulting potential clinical advantage is the enhanced surgical versatility associated with selecting for implantation either a resurfacing or posterior stabilized condylar-type of total knee prosthesis with the same femoral and tibial bone resection preparation. Additionally, in the event surgical revision is indicated, due to joint instability considerations, revision of the femoral component from a resurfacing-type to a posterior stabilized-type can be more easily accomplished, since the bone cuts for either prosthetic device are the same, contrary to conventional posterior stabilized knee prostheses.

In still another preferred embodiment, the UHMWPE tibial bearing component for the posterior stabilized knee prosthesis is essentially identical to its condylar resurfacing-type counterpart in all features, except for the addition of the interconnecting projection, which incorporates the follower bearing surface. The tibial component of posterior stabilizer design, therefore, can also be employed with a (non-stabilizing) condylar-type of resurfacing femoral component, provided that design consistency of the femoro-tibial bearing surfaces, component size and posterior cruciate clearance is maintained. This potential dual functionally with both types of femoral components could result in less system complexity and reduced implant inventory requirements. Surgical instrumentation can also be simplified, since the posterior stabilized provisional tibial trial components could accommodate the non-stabilized resurfacing-type of knee, as well. Tibial provisional trial components, generally available in numerous bearing thicknesses to address a relatively wide range of tibial bone resection levels, are used to assess prosthetic joint function prior to finalization of implant component selection and fixation. This functional commonality, therefore, can result in a significant reduction in the quantity of tibial trials required.

In accordance with an aspect of the present invention, a posterior stabilized knee prosthesis comprises a femoral component including a medial condyle having an anterior portion, a distal portion and a posterior portion, a lateral condyle having an anterior portion, a distal portion and a posterior portion, an anterior patella flange interconnecting the anterior portions of the medial and lateral condyles in parallel, spaced apart relation, and a cam member connected to the lateral surface of the posterior portion of the medial condyle and to the medial surface of the posterior portion of the lateral condyle, the cam member having a convex cam surface; a tibial component including multi-radius tibial plateau bearing surface means for receiving the medial and lateral condyles for rolling and sliding movement thereon, and follower member means for receiving the convex cam surface of the cam member for rolling and sliding movement thereon, the follower member means being connected with the bearing surfaces; and the convex cam surface being in contact with the follower member means for substantially the entire flexion range of the knee.

In accordance with another aspect of the present invention, a posterior stabilized knee prosthesis comprises a femoral component including a medial condyle having an anterior portion, a distal portion and a posterior portion, a lateral condyle having an anterior portion, a distal portion and a posterior portion, an anterior patella flange interconnecting the anterior portions of the medial and lateral condyles in parallel, spaced apart relation, and a cam member connected to the lateral surface of the posterior portion of the medial condyle and to the medial surface of the posterior portion of the lateral condyle, the cam member having a convex cam surface; a tibial component including multi-radius tibial plateau bearing surface means for receiving the medial and lateral condyles for rolling and sliding movement thereon, and follower member means for receiving the convex cam surface of the cam member for rotational and sliding movement thereon, the follower member means being connected with the bearing surfaces; and the convex cam surface being in sliding contact with the follower member means to provide posterior rollback of said condyles on said tibial plateau bearing surface means during flexion, starting at approximately hyperextension flexion, and being completed at an angle less than approximately 40° of maximum normal flexion.

In accordance with still another aspect of the present invention, a posterior stabilized knee prosthesis comprises a femoral component including a medial condyle having an anterior portion, a distal portion and a posterior portion, a lateral condyle having an anterior portion, a distal portion and a posterior portion, an anterior patella flange interconnecting the anterior portions of the medial and lateral condyles in parallel, spaced apart relation, and a cam member connected to the lateral surface of the posterior portion of the medial condyle and to the medial surface of the posterior portion of the lateral condyle, the cam member having a convex cam surface; a tibial component including multi-radius tibial plateau bearing surface means for receiving the medial and lateral condyles for rolling and sliding movement thereon, and follower member means for receiving the convex cam surface of the cam member for rotational and sliding movement thereon, the follower member means being connected with the bearing surfaces; and the convex cam surface being in congruent contact with the follower member means from approximately the end of posterior rollback to full flexion.

The above and other objects, features and advantages of the present invention will become apparent from the following detailed description of the invention when considered in conjunction with the accompanying drawings.

BRIEF DESCRIPTION OF THE DRAWINGS

FIG. 1 is a front (anterior) elevational view of a posterior stabilized knee prosthesis according to a first embodiment of the present invention, in which the femoral component is in contact with the tibial component and in which the left side is the lateral aspect and the right side is the medial aspect;

FIG. 2 is a medial side elevational view of the knee prosthesis of FIG. 1, with the anterior aspect being to the left and the posterior aspect being to the right of the drawing;

FIG. 3 is a top plan view of the femoral component of the knee prosthesis of FIG. 1, showing the slotted intercondylar posterior stabilizer cam member, and with the anterior aspect being to the left and the posterior aspect being to the right of the drawing;

FIG. 4 is a rear (posterior) view of the knee prosthesis of FIG. 1, with the femoral component shown separated from the tibial component and with the right side of the drawing being lateral;

FIG. 5 is a bottom plan view of the femoral component of FIG. 3, with the upper side of the drawing being anterior and the lower side of the drawing being posterior;

FIG. 6 is a cross-sectional view of the knee prosthesis of FIG. 4 in assembled condition, taken along line 6—6 thereof, showing the relative positions of the cam and follower members at the onset of flexion (maximum hyperextension), and with the anterior aspect being to the left and the posterior aspect being to the right of the drawing;

FIG. 7 is a cross-sectional view of the knee prosthesis of FIG. 1, taken along line 7—7 thereof, showing the relative position of the anterior-distal femoral condyle and anterior aspect of the concave tibial plateau bearing surface at maximum hyperextension, and with the anterior aspect being to the left and the posterior aspect being to the right of the drawing;

FIG. 8 is a top plan view of the UHMWPE tibial plateau of the tibial component of the knee prosthesis of FIG. 1, showing the medial and lateral femoro-tibial plateau bearing surfaces and the interconnecting projection and integral stabilizer follower member, and with the anterior aspect being to the left and the posterior aspect being to the right of the drawing;

FIG. 9 is a bottom plan view of the porous coated bone side of the tibial component of FIG. 8, with the upper side of the drawing being anterior and the lower side of the drawing being posterior;

FIGS. 10A–10D are partial cross-sectional views similar to FIG. 6, showing flexing of the knee from maximum hyperextension to full flexion;

FIG. 11 is a top plan view similar to FIG. 8, of an UHMWPE tibial plateau bearing component of a tibial component according to another embodiment of the present invention, with a posterior cruciate cut-out section;

FIG. 12 is a cross-sectional view similar to FIG. 6, of the femoral component of FIGS. 1–10 with a slotted intercondylar posterior stabilizer cam member, in contact with the tibial component of FIG. 11;

FIG. 13 is a bottom plan view of the metal tibial base plate of the tibial component of FIG. 11, with the posterior cruciate cut-out section;

FIG. 14 is a top plan view similar to FIG. 3, of a femoral component of a knee prosthesis according to still another embodiment of the present invention, with a continuous intercondylar posterior stabilizer cam member;

FIG. 15 is a rear (posterior) view of the femoral component of the knee prosthesis of FIG. 14;

FIG. 16 is a bottom plan view of the femoral component of FIG. 14;

FIG. 17 is a top plan view of the UHMWPE tibial plateau of the tibial component of the knee prosthesis of FIG. 14;

FIG. 18 is a cross-sectional view of the knee prosthesis of FIG. 14 in assembled condition, taken along line 18—18 thereof;

FIG. 19 is a top plan view similar to FIG. 3, of a femoral component of a knee prosthesis according to yet another embodiment of the present invention, with a continuous and extended intercondylar posterior stabilizer cam member;

FIG. 20 is a rear (posterior) view of the femoral component of the knee prosthesis of FIG. 19;

FIG. 21 is a bottom plan view of the femoral component of FIG. 19;

FIG. 22 is a top plan view of the UHMWPE tibial plateau of the tibial component of the knee prosthesis of FIG. 19;

FIG. 23 is a cross-sectional view of the knee prosthesis of FIG. 19 in assembled condition, taken along line 23—23 thereof;

FIG. 24 is a top plan view similar to FIG. 3, of a femoral component of a knee prosthesis according to yet another embodiment of the present invention, with a slotted and extended intercondylar posterior stabilizer cam member;

FIG. 25 is a rear (posterior) view of the femoral component of the knee prosthesis of FIG. 24;

FIG. 26 is a bottom plan view of the femoral component of FIG. 24;

FIG. 27 is a top plan view of the UHMWPE tibial plateau of the tibial component of the knee prosthesis of FIG. 24;

FIG. 28 is a cross-sectional view of the knee prosthesis of FIG. 24 in assembled condition, taken along line 28—28 thereof;

FIG. 29A is a front (anterior) elevational view, similar to FIG. 1, of the posterior stabilized knee prosthesis of FIG. 24; and FIGS. 29B-29E are partial cross-sectional views similar to FIGS. 10A-10D, showing flexing of the knee from maximum hyperextension to full flexion with the knee prosthesis of FIG. 24.

DETAILED DESCRIPTION OF THE PREFERRED EMBODIMENTS

The present invention pertains to a posterior stabilized total knee prosthesis, which provides posterior tibial-to-femoral constraint, throughout the entire range of flexion and extension; thus, reducing the possibility of anterior dislocation of the distal femur in clinical situations involving an incompetent or absent posterior cruciate ligament or posterior tibial instability. In this regard, it is categorized as a totally posterior stabilized total knee prosthesis device. This is accomplished without the need of a cumbersome "stabilizer box", which must be accommodated by a substantial box-like resection of viable bone from within the intercondylar sector of the distal femur.

Further, the stabilizer cam/follower members are specially designed to provide natural-like posterior rollback of the femoro-tibial articulation, commencing at the start of flexion or maximum hyperextension (at about $-6°$ flexion) and completing at about $25°-30°$ flexion. From this point in the flexion range to full-flexion, both the cam/follower members and the femoro-tibial articular bearings attain a state of congruent contact, which minimizes contact stress. Attainment of this design condition also provides anterior (tibial-to-femoral) constrainment, thus reducing the possibility of posterior dislocation of the distal femur.

Additionally, the posterior stabilizer mechanism functions in concert with the medial and lateral femoro-tibial bearings to sustain, transfer and distribute the resultant compressive knee joint reaction forces, during flexion, to the underlying fixation surfaces and adjacent supportive bone structure. The net effective contact area of the cam/follower mechanism of the present invention increases as flexion angle increases, therefore tending to maintain a more uniform level of contact stress at the associated higher levels of joint loading, than other posterior stabilizing knee prosthesis designs that do not incorporate congruent articular contact.

Referring now to FIGS. 1-9, a totally posterior stabilized knee prosthesis 10 according to a first embodiment of the present invention includes a metallic alloy femoral component 12 and a corresponding tibial component 14. Femoral component 12 incorporates multi-radius medial and lateral condylar runners or condyles 16 and 18 which mimic the natural femoral condyles of the distal femur, which they replace. Specifically, medial and lateral condyles 16 and 18 include three distinct portions, that is, respective posterior portions 20 and 22, distal portions 24 and 26, and anterior portions 28 and 30.

In addition, femoral component 12 includes a convex cam member 32 of the posterior stabilizer mechanism, positioned in an intercondylar location between the distal portions 24 and 26 and between the posterior portions 20 and 22 of medial and lateral condyles 16 and 18, respectively. As shown in the first embodiment of FIGS. 1-9, cam member 32 is formed in two parts 33a and 33b, each integral with and extending from the inner edge of condyles 16 and 18 toward each other, with a gap 34 therebetween. Further, the radius of curvature $r_1$ of cam member 32 is identical with the radius of curvature $r_1$ of the posterior portions 20 and 22 of medial and lateral condyles 16 and 18, with the centers of curvature located at points $O_c$ and $O_p$ respectively, as shown in FIGS. 2, 6 and 7.

The anterior portion of femoral component 12 is formed of the aforementioned anterior portions 28 and 30 of medial and lateral condyles 16 and 18, and an anterior patella flange 36 integral with and interconnecting anterior portions 28 and 30 of medial and lateral condyles 16 and 18. The patella member (not shown) articulates with anterior patella flange 36 biased laterally at the outset of flexion and transfers articulation to distal aspects of the anterior portions 28 and 30 at approximately $25°$ flexion. From this point on in the flexion cycle, the patella-femoral joint articulation occurs at the inside corners 38 (FIG. 1) of distal portions 24 and 26, as the flexion angle increases to full-range. It is noted that the inside surfaces of femoral component 12 which interface directly with bone in the biological bone-ingrowth fixation mode or with an interpositional thickness of poly-methyl-methacrylate (PMMA) bone cement in the cemented mode, are the anterior inner surface 40, the inner anterior-distal surface 42, the inner medial and lateral distal surfaces 44 and 46, the inner medial and lateral distal-posterior surfaces 48 and 50, and the inner medial and lateral posterior surfaces 52 and 54. These surfaces may incorporate an integral sintered, diffusion bonded or plasma sprayed porous surface structure 56, only a portion of which is shown in FIG. 3, as a component biological or cemented fixation means. In addition, upwardly extending cylindrical posts 55 are provided which fit into holes formed in the distal end of the femur to aid in the fixation stability of femoral component with the femur.

In accordance with the present invention, as will be explained in greater detail hereinafter, the maximum height of the central tibial projection does not extend beyond the thickness of the distal portions 24 and 26 and posterior portions 20 and 22 of medial and lateral condyles 16 and 18, at the level of the inside (bone-side) surface of inner distal surfaces 44 and 46 and inner posterior surfaces 52 and 54. Therefore, a stabilizer box structure, common to most other posterior stabilizing total knee designs, is not required. As a result, accommodation of the femoral component by resecting a significant "block" of viable bone from the intercondylar sector of the distal femur is not required by the present invention.

Further, an intercondylar opening 37 within the condyles 16 and 18 is formed by the posterior edge 29 of anterior patellar flange 36, the anterior aspects 32a of the intercondylar stabilizer cam member 32, and the medial and lateral edges 16a and 18a of the respective lateral and medial condyles 16 and 18. The boundaries of opening 37 are essentially within the plane and maximum thickness of the distal or posterior portions of femoral condyles 16 and 18. However, an intercondylar stabilizer box which protrudes within the bone space of the distal femur and requiring a substantial removal of bone to provide the necessary clearance for implantation is not required by the present invention.

The UHMWPE tibial component 14 includes equispaced concave multi-radius medial and lateral tibial plateau bearing surfaces 58 and 60 which receive convex multi-radius medial and lateral femoral condyles 16 and 18 for articulation thereon. In like manner to condyles 16 and 18, and because of the convex multi-radius shape of tibial plateau bearing surfaces 58 and 60, it will be appreciated that tibial plateau bearing surfaces 58 and 60 include posterior portions 62 and 64, distal portions 66 and 68, and anterior portions 70 and 72, respectively. Between medial and lateral tibial plateau bearing surfaces 58 and 60, tibial component 14 includes an anterior-central tibial plateau bearing projection 74 interconnecting medial and lateral anterior portions 70 and 72 of medial and lateral tibial plateau bearing surfaces 58 and 60, respectively. During the early stages of flexion, anterior-central tibial plateau bearing projection 74 is positioned between the inside corners 38 of distal portions 24 and 26 of medial and lateral condyles 16 and 18, respectively, as shown best in FIG. 1, providing medial-lateral and axial rotational knee constraint. The degree of translational and rotational freedom is a function of the dimensional clearances between distal portions 24 and 26 of medial and lateral condyles 16 and 18, and the anterior portion of projection 74. As the flexion angle increases, posterior portions 20 and 22 of medial and lateral condyles 16 and 18 span the anterior portion of projection 74. At maximum hyperextension, the anterior aspects of distal portions 24 and 26 of medial and lateral condyles 16 and 18 contact the anterior portions 70 and 72 of medial and lateral tibial plateau bearing surfaces 58 and 60, respectively, which provides posterior (tibia-to-femur) stabilization or constraint to prevent anterior subluxation or dislocation of the femur.

In addition, tibial component 14 includes a follower member 76 which is in bearing contact with cam member 32, in a manner which will be described in greater detail hereinafter. Follower member 76 includes an arcuate medial and lateral concave follower bearing surface 78, which extends beyond mid-line line 82 of tibial component 14 for mating with the distal surfaces of cam member 32. Furthermore, partition member 79 is adapted to fit within gap 34 of cam member 32. It will be appreciated that the radius of curvature $r_2$ of follower member 76 is the same as the radius of curvature of posterior portions 62 and 64 of medial and lateral tibial plateau bearing surfaces 58 and 60, respectively, with the centers of curvature located at $O_f$ and $O_t$, respectively.

At maximum hyperextension or the earliest stage of knee flexion, the anterior aspects 32a of cam parts 33a and 33b of stabilizer cam member 32 contact follower member 76 at the upward sloping bearing surface 78a, slightly anterior of the mid-line 82 (FIG. 8). This contact between cam member 32 and follower member 76 represents the earliest stages of posterior (tibia-to-femur) stabilization, which occurs at maximum hyperextension or the earliest stage of knee flexion. As the flexion angle increases, the camming action between the initial non-congruent contact of the anterior aspects 32a of cam member 32 and the upward sloping concave portion 78a of follower bearing surface 78 of follower member 76 causes the center of curvature $O_c$ of cam member 32 to displace posteriorly and approach the center of curvature $O_f$ of follower member 76, therefore allowing the femoral condyles 16 and 18 to translate posteriorly.

This posterior rollback of the femur-tibial articular contact continues up to approximately 25°–30° flexion, where both the center of curvature $O_c$ of cam member 32 and the center of curvature $O_f$ of follower member 76 coincide. When this occurs, the convex articular surface of cam member 32 and the posterior portion 78b of the concave articular bearing surface 78 of follower member 76 come into intimate or congruent contact, as shown best in FIG. 10B. Since the center of curvature $O_c$ of cam member 32 is identical to the center of curvature $O_p$ of the posterior portions 20 and 22 of medial and lateral condyles 16 and 18, and similarly, the radius of curvature $O_f$ of follower member 76 is identical to the radius of curvature $O_t$ of posterior portions 62 and 64 of medial and lateral tibial plateau bearing surfaces 58 and 60, both the stabilizer cam-follower and condylar femoro-tibial articular surfaces come into congruent contact simultaneously, at 25°–30° flexion, when posterior rollback is completed. From this point on, until full flexion is reached, cam member 32 and follower member 76 of the posterior stabilizer mechanism functions to (1) provide posterior (tibia-to-femur) stabilization to deter anterior subluxation and dislocation of the distal femur and (2) sustain and distribute the compressive joint reaction forces during flexion in conjunction with the medial and lateral femoro-tibial joint bearing surfaces.

Preferably, the tibial component 14 is formed by a UHMWPE tibial plateau bearing component or insert 57 which is assembled and interlocked onto a metallic alloy tibial base component 84. The underside 86 of tibial base component 84 may incorporate an integral sintered or diffusion bonded metallic alloy porous surface structure 88 as a cemented or as a biological ingrowth bone fixation means, and may incorporate short integral peg stabilizers 90 for augmented torsional and translational bone/prosthesis fixational constraint.

As shown in FIGS. 10A-10D, the contact mechanics of the cam-follower mechanism, as well as the femorotibial joint, can be followed at various stages in the flexion cycle. At the outset of flexion (maximum hyperextension), as shown in FIGS. 6 and 10A, the anterior aspect 32a of cam member 32 contacts the upwardly sloping concave portion 78a of concave follower bearing surface 78 of follower member 76, at a point slightly anterior of the follower mid-line 82. The anterior aspects of distal portions 24 and 2 of medial and lateral condyles 16 and 18 congruently contact the anterior aspects of medial and lateral tibial plateau bearing surfaces 70 and 72, respectively, which also provides posterior stabilization of the reconstructed knee joint at maximum hyperextension. As flexion continues, the anterior aspects 32a of cam member 32 contact the upwardly sloping concave portion 78a of follower member 76, as shown in FIG. 10A, and produces a camming action which causes the center of curvature $O_c$ of cam member 32 to be displaced, posteriorally and toward the center of curvature $O_f$ of follower member 76. At approximately 25°-30° flexion, the center of curvature $O_c$ of cam member 32 and the center of curvature $O_f$ of follower member 76 coincide, allowing cam member 32 and follower member 76 to come into complete or congruent contact, as shown in FIG. 10B. At this point, the posterior portions 20 and 22 of medial and lateral condyles 16 and 18, and the posterior portions 62 and 64 of the medial and lateral tibial plateau bearing surfaces 58 and 60 also come into congruent contact. As the flexion angle increases, the cam-follower articular bearing surface and the femoro-tibial articular bearing surface remain in congruent contact. The net area of contact of the cam-follower mechanism, however, which increases proportionally with flexion angle, attains maximum contact area at about 60° flexion, as shown in FIG. 10C. From this point in the flexion range, to full flexion, the net area of the cam-follower mechanism gradually decreases to about half of the total available area, as shown in FIG. 10D.

It will be appreciated that various modifications can be made to the present invention within the scope of the claims herein.

For example, as shown in FIGS. 11-13, a knee prosthesis 110 according to another embodiment of the present invention is shown, in which elements corresponding to those of knee prosthesis 10 of FIGS. 1-10 are identified by the same reference numerals augmented by 100, and a detailed description thereof is omitted herein for the sake of brevity. Specifically, with knee prosthesis 110, tibial component 14 is provided with a posterior cruciate cut-out section 192. Thus, the tibial component for the present posterior stabilized knee prosthesis can provide dual functionality, since it can also be used to provide the required tibial bearing surface with posterior cruciate retention, that is, to provide clearance for the posterior cruciate ligaments for a resurfacing type of knee construction or for the present posterior stabilized knee prosthesis.

Although knee prostheses 10 and 110 have been shown with slotted articular surface designs for the cam members, it will be appreciated that the present invention can be utilized with a continuous articular surface design. In this regard, a knee prosthesis 210 according to another embodiment of the present invention is shown in FIGS. 14-18, in which elements corresponding to those identified with respect to knee prosthesis 10 of FIGS. 1-10 are identified by the same reference numerals augmented by 200, and a detailed description thereof is omitted herein for the sake of brevity. Specifically, with knee prosthesis 210, gap 34 between cam parts 33a and 33b of cam member 32 is eliminated, and, in place thereof, cam parts 33a and 33b are connected together to form a continuous cam surface 232. In all other respects, knee prosthesis 210 is identical to knee prosthesis 10 of FIGS. 1-10.

Knee prosthesis 210 has the advantage that the extended cam surface allows retention of a larger contact area of the posterior stabilizer mechanism in the flexion range of about 25°-30° to full-flexion, as opposed to the slotted cam configuration of FIGS. 1-10, which straddles the posterior portion 79 of the central tibial projection or eminence 74 throughout the entire range of flexion to provide translational and rotational constraint at the higher end of the flexion range, when required.

Referring now to FIGS. 19-23, a posterior stabilized total knee prosthesis 310 according to another embodiment of the present invention is shown, in which elements corresponding to those identified with respect to knee prosthesis 210 of FIGS. 14-18 are identified by the same reference numerals, augmented by 100, and a detailed description thereof is omitted herein for the sake of brevity. Knee prosthesis 310 differs from knee prosthesis 210 in that cam member 332 is extended to incorporate the same sectional geometry as the medial and lateral posterior condyles 20 and 22. The extended cam surface allows retention of maximum contact area of the posterior stabilizer mechanism in the flexion range of about 25°-30° to full-flexion.

Referring now to FIGS. 24-28 and 29A, a posterior stabilized total knee prosthesis 410 according to another embodiment of the present invention is shown, in which elements corresponding to those of knee prosthesis 10 of FIGS. 1-10 are identified by the same reference numerals, augmented by 400, and a detailed description thereof is omitted herein for the sake of brevity. Total knee prosthesis 410 combines the attributes of total knee prosthesis 10 of FIGS. 1-10 and total knee prosthesis 310 of FIGS. 19-23 by providing a slotted and extended intercondylar posterior stabilizer cam member 432. As with the embodiment of FIGS. 19-23, the extended cam surface allows retention of maximum contact area of the posterior stabilizer mechanism in the flexion range of about 25°-30° to full-flexion, and in addition, the slotted cam configuration straddles the posterior portion 479 of the central tibial eminence 474 throughout the entire range of flexion to provide translational and rotational constraint at the higher end of the flexion range, when required.

As shown in FIGS. 29B-29E, the contact mechanics of the cam-follower mechanism, as well as the femorotibial joint, can be followed at various stages in the flexion cycle for knee prosthesis 410. In this regard, the flexion cycle corresponds to that of FIGS. 10A-10D.

At the outset of flexion (maximum hyperextension), as shown in FIG. 29B, the anterior aspect 432a of cam member 432 contacts the upwardly sloping concave portion 478a of concave follower bearing surface 478 of follower member 476, at a point slightly anterior of the follower mid-line. The anterior aspects of distal portions 424 and 426 of medial and lateral condyles 416 and 418 congruently contact the anterior aspects of medial and lateral tibial plateau bearing surfaces 470 and 472, respectively, at this time, which also provides posterior stabilization of the reconstructed knee joint at maximum hyperextension. As flexion continues, the anterior aspect 432a of cam member 432 contacts the upwardly sloping concave portion 478a of follower member 476, as shown in FIG. 29B, and produces a camming action which causes the center of curvature of cam member 432 to be displaced, posteriorly and toward the center of curvature of follower member 476. At approximately 25°-30° flexion, the center of curvature of cam member 432 and the center of curvature of follower member 476 coincide, allowing cam member 432 and follower member 476 to come into complete or congruent contact, as shown in FIG. 29C. At this point, the posterior portions 420 and 422 of medial and lateral condyles 416 and 418, and the posterior portions 462 and 464 of medial and lateral tibial plateau bearing surfaces 458 and 460 also come into congruent contact. As the flexion angle increases, the cam-follower articular bearing surface and the femoro-tibial articular bearing surface remain in congruent contact. The net area of contact of the cam-follower mechanism increases proportionately with flexion angle, attaining maximum contact area at about 60° flexion. However, unlike knee prosthesis 10, knee prosthesis 410 maintains this maximum contact area through the full range of flexion, as shown in FIG. 29E.

It will be appreciated that various changes can be incorporated into the present invention as claimed. For example, an intramedullary stem can be added to the tibial and/or femoral components.

Having described specific preferred embodiments of the preferred invention with reference to the accompanying drawings, it will be appreciated that the present invention is not limited to those precise embodiments, and that various changes and modifications can be effected therein by one of ordinary skill in the art without departing from the spirit or scope of the invention as defined by the appended claims.

What is claimed is:

1. A posterior stabilized knee prosthesis comprising:
   a) a femoral component including:
      i) a medial condyle having an anterior portion, a distal portion and a posterior portion;
      ii) a lateral condyle having an anterior portion, a distal portion and a posterior portion;
      iii) an anterior patella flange interconnecting the anterior portions of the medial and lateral condyles in parallel, spaced apart relation; and
      iv) a cam member connected to the lateral surface of the posterior portion of said medial condyle and to the medial surface of the posterior portion of said lateral condyle, said cam member having a convex cam surface;
   b) a tibial component including:
      i) multi-radius tibial plateau bearing surface means for receiving said medial and lateral condyles for rolling and sliding movement thereon; and
      ii) follower member means for receiving said convex cam surface of said cam member for rotational and sliding movement thereon, said follower member means being connected with said bearing surface means; and
   c) said knee prosthesis having a flexion range, with said convex cam surface being in contact with said follower member means for substantially the entire flexion range.

2. A posterior stabilized knee prosthesis according to claim 1, wherein said medial and lateral condyles have inner fixation surfaces for fixing said femoral component to the distal end of a femur, and said cam member and said follower member means have heights which are not higher than boundaries of said inner fixation surfaces.

3. A posterior stabilized knee prosthesis according to claim 1, wherein said cam surface has a center of curvature and said posterior portions of said medial and lateral condyles each have a center of curvature, with the center of curvature of said cam surface being substantially the same as the centers of curvature of said posterior portions of said medial and lateral condyles.

4. A posterior stabilized knee prosthesis according to claim 3, wherein said tibial plateau bearing surface means includes a multi-radius medial tibial plateau bearing surface for receiving the medial condyle for rolling and sliding movement thereon, and a multi-radius lateral tibial plateau bearing surface for receiving the lateral condyle for rolling and sliding movement thereon, wherein each of said multi-radius medial and lateral tibial plateau bearing surfaces includes an anterior portion and a posterior portion, said anterior portions being connected together by a tibial plateau bearing projection, wherein said follower member means has a center of curvature and said posterior portions of said medial and lateral tibial plateau bearing surfaces each include a center of curvature which is substantially the same as the center of curvature of the follower member means.

5. A posterior stabilized knee prosthesis according to claim 1, wherein said cam member includes a medial cam part connected with the lateral surface of the posterior portion of said medial condyle and a lateral cam part connected with the medial surface of the posterior portion of said lateral condyle.

6. A posterior stabilized knee prosthesis according to claim 5, wherein said medial and lateral cam parts are spaced apart by a gap therebetween.

7. A posterior stabilized knee prosthesis according to claim 6, wherein said follower member means is formed with a partition which fits within said gap.

8. A posterior stabilized knee prosthesis according to claim 1, wherein said cam member extends substantially to a posterior end of said posterior portions of said medial and lateral condyles.

9. A posterior stabilized knee prosthesis according to claim 1, wherein said tibial plateau bearing surface means includes a multi-radius medial tibial plateau bearing surface for receiving the medial condyle for rolling and sliding movement thereon, and a multi-radius lateral tibial plateau bearing surface for receiving the lateral condyle for rolling and sliding movement thereon.

10. A posterior stabilized knee prosthesis according to claim 9, wherein each of said multi-radius medial and lateral tibial plateau bearing surfaces includes an anterior portion and a posterior portion, said anterior portions being connected together by a tibial plateau bearing projection.

11. A posterior stabilized knee prosthesis according to claim 10, wherein said follower member means has a radius of curvature and said posterior portions of said medial and lateral tibial plateau bearing surfaces each include a radius of curvature which is substantially the same as the radius of curvature of the follower member means.

12. A posterior stabilized knee prosthesis according to claim 10, wherein said tibial plateau bearing projection leads into said follower member means.

13. A posterior stabilized knee prosthesis according to claim 10, wherein said follower member means is formed as a continuous section between said posterior portions of said multi-radius medial and lateral tibial plateau bearing surfaces.

14. A posterior stabilized knee prosthesis according to claim 1, wherein said tibial component includes a posterior recess.

15. A posterior stabilized knee prosthesis according to claim 1, wherein said tibial component includes a tibial plateau bearing component containing said multi-radius tibial plateau bearing surface means and said follower member means, and a tibial base component connected to an underside of said tibial plateau bearing component.

16. A posterior stabilized knee prosthesis according to claim 1, wherein said cam surface and follower member means each have a radius of curvature; wherein said posterior portions of said medial and lateral condyles each have a radius of curvature; wherein said tibial plateau bearing surface means includes a multi-radius medial tibial plateau bearing surface for receiving the medial condyle for rolling and sliding movement thereon, and a multi-radius lateral tibial plateau bearing surface for receiving the lateral condyle for rolling and sliding movement thereon; wherein each of said multi-radius medial and lateral tibial plateau bearing surfaces includes an anterior portion and a posterior portion, said anterior portions being connected together by a tibial plateau bearing projection; wherein said posterior portions of said medial and lateral tibial plateau bearing surfaces each include a radius of curvature which is substantially the same as the radius of curvature of the posterior portions of said medial and lateral condyles; wherein the radius of curvature of the follower member means is substantially the same as the radius of curvature of the cam surface but less than the radius of curvature of the medial and lateral condyles.

17. A posterior stabilized knee prosthesis according to claim 1,
with said convex cam surface being in sliding contact with said follower member means to provide posterior rollback of said condyles on said tibial plateau bearing surface means during flexion, starting at approximately −6° flexion, and being completed at an angle less than approximately 40° of flexion.

18. A posterior stabilized knee prosthesis according to claim 17, wherein said medial and lateral condyles have inner fixation surfaces for fixing said femoral component to the distal end of a femur, and said cam member and said follower member means have heights which are not higher than boundaries of said inner fixation surfaces.

19. A posterior stabilized knee prosthesis according to claim 17, wherein said cam surface has a center of curvature and said posterior portions of said medial and lateral condyles each have a center of curvature, with the center of curvature of said cam surface being substantially the same as the centers of curvature of said posterior portions of said medial and lateral condyles.

20. A posterior stabilized knee prosthesis according to claim 17, wherein said cam member includes a medial cam part connected with the lateral surface of the posterior portion of said medial condyle and a lateral cam part connected with the medial surface of the posterior portion of said lateral condyle.

21. A posterior stabilized knee prosthesis according to claim 20, wherein said medial and lateral cam parts are spaced apart by a gap therebetween.

22. A posterior stabilized knee prosthesis according to claim 19, wherein said follower member means is formed with a partition which fits within said gap.

23. A posterior stabilized knee prosthesis according to claim 17, wherein said cam member extends substantially to a posterior end of said posterior portions of said medial and lateral condyles.

24. A posterior stabilized knee prosthesis according to claim 17, wherein said tibial plateau bearing surface means includes a multi-radius medial tibial plateau bearing surface for receiving the medial condyle for rolling and sliding movement thereon, and a multi-radius lateral tibial plateau bearing surface for receiving the lateral condyle for rotational and sliding movement thereon.

25. A posterior stabilized knee prosthesis according to claim 24, wherein each of said multi-radius medial and lateral tibial plateau bearing surfaces includes an anterior portion and a posterior portion, said anterior portions being connected together by a tibial plateau bearing projection.

26. A posterior stabilized knee prosthesis according to claim 25, wherein said follower member means has a radius of curvature and said posterior portions of said medial and lateral tibial plateau bearing surfaces each include a radius of curvature which is substantially the same as the radius of curvature of the follower member means.

27. A posterior stabilized knee prosthesis according to claim 25, wherein said tibial plateau bearing projection leads into said follower member means.

28. A posterior stabilized knee prosthesis according to claim 25, wherein said follower member means is formed as a continuous section between said posterior portions of said multi-radius medial and lateral tibial plateau bearing surfaces.

29. A posterior stabilized knee prosthesis according to claim 17, wherein said tibial component includes a posterior recess.

30. A posterior stabilized knee prosthesis according to claim 17, wherein said tibial component includes a tibial plateau bearing component containing said multi-radius tibial plateau bearing surface means and said follower member means, and a tibial base component connected to an underside of said tibial plateau bearing component.

31. A posterior stabilized knee prosthesis according to claim 17, wherein said posterior rollback is completed at approximately 25°-30° of flexion.

32. A posterior stabilized knee prosthesis according to claim 1,
with said convex cam surface being in congruent contact with said follower member means from approximately an end of posterior rollback, of from 25°-30° flexion, between the cam surface and follower member means, to full flexion.

33. A posterior stabilized knee prosthesis according to claim 32, wherein said medial and lateral condyles have inner fixation surfaces for fixing said femoral component to the distal end of a femur, and said cam member and said follower member means have heights which are not higher than boundaries of said inner fixation surfaces.

34. A posterior stabilized knee prosthesis according to claim 32, wherein said cam surface has a center of curvature and said posterior portions of said medial and lateral condyles each have a center of curvature, with the centers of curvature of said cam surface being substantially the same as the center of curvature of said posterior portions of said medial and lateral condyles.

35. A posterior stabilized knee prosthesis according to claim 32, wherein said cam member includes a medial cam part connected with the lateral surface of the posterior portion of said medial condyle and a lateral cam part connected with the medial surface of the posterior portion of said lateral condyle.

36. A posterior stabilized knee prosthesis according to claim 35, wherein said medial and lateral cam parts are spaced apart by a gap therebetween.

37. A posterior stabilized knee prosthesis according to claim 34, wherein said follower member means is formed with a partition which fits within said gap.

38. A posterior stabilized knee prosthesis according to claim 32, wherein said cam member extends substantially to a posterior end of said posterior portions of said medial and lateral condyles.

39. A posterior stabilized knee prosthesis according to claim 32, wherein said tibial plateau bearing surface means includes a multi-radius medial tibial plateau bearing surface for receiving the medial condyle for rolling and sliding movement thereon, and a multi-radius lateral tibial plateau bearing surface for receiving the lateral condyle for rolling and sliding movement thereon.

40. A posterior stabilized knee prosthesis according to claim 39, wherein each of said multi-radius medial and lateral tibial plateau bearing surfaces includes an anterior portion and a posterior portion, said anterior portions being connected together by a tibial plateau bearing projection.

41. A posterior stabilized knee prosthesis according to claim 40, wherein said follower member means has a radius of curvature and said posterior portions of said medial and lateral tibial plateau bearing surfaces each include a radius of curvature which is substantially the same as the radius of curvature of the follower member means.

42. A posterior stabilized knee prosthesis according to claim 40, wherein said tibial plateau bearing projection leads into said follower member means.

43. A posterior stabilized knee prosthesis according to claim 40, wherein said follower member means is formed as a continuous section between said posterior portions of said multi-radius medial and lateral tibial plateau bearing surfaces.

44. A posterior stabilized knee prosthesis according to claim 32, wherein said tibial component includes a posterior recess.

45. A posterior stabilized knee prosthesis according to claim 32, wherein said tibial component includes a tibial plateau bearing component containing said multi-radius tibial plateau bearing surface means and said follower member means, and a tibial base component connected to an underside of said tibial plateau bearing component.

46. A posterior stabilized knee prosthesis according to claim 32, wherein said cam surface has a radius of curvature and said posterior portions of said medial and lateral condyles each have a radius of curvature, with the radius of curvature of said cam surface being substantially the same as the radius of curvature of said posterior portions of said medial and lateral condyles, wherein said tibial plateau bearing surface means includes a multi-radius medial tibial plateau bearing surface for receiving the medial condyle for rolling and sliding movement thereon, and a multi-radius lateral tibial plateau bearing surface for receiving the lateral condyle for rolling and sliding movement thereon, wherein each of said multi-radius medial and lateral tibial plateau bearing surfaces includes an anterior portion and a posterior portion, said anterior portions being connected together by a tibial plateau bearing projection, wherein said follower member means has a radius of curvature and said posterior portions of said medial and lateral tibial plateau bearing surfaces each include a radius of curvature which is substantially the same as the radius of curvature of the follower member means, and wherein the radius of curvature of the follower member means is substantially the same as the radius of curvature of the cam surface.

* * * * *